United States Patent [19]

Miles et al.

[11] Patent Number: 4,477,578
[45] Date of Patent: Oct. 16, 1984

[54] METHOD AND APPARATUS FOR PERFORMING ASSAYS

[75] Inventors: Laughton E. Miles, Stanford; Arthur H. Rogers, Jr., Los Altos, both of Calif.; Charles H. Rogers, Duxbury, Mass.

[73] Assignee: Medical & Scientific, Inc., Rockland, Mass.

[21] Appl. No.: 354,848

[22] Filed: Mar. 4, 1982

[51] Int. Cl.³ .................. G01N 33/54; G01N 33/56; G01N 35/04; G01N 35/06
[52] U.S. Cl. .................. 436/518; 73/864.01; 141/1; 141/5; 141/51; 118/50; 422/64; 422/68; 422/100; 422/102; 422/61; 422/67; 422/71; 436/500; 436/501; 436/513; 436/527; 436/548; 436/545; 436/542; 436/807; 436/808; 436/810; 436/847; 436/57; 436/178; 436/180; 436/820
[58] Field of Search ........... 73/864.01; 118/50, 408, 118/421, 667, 693; 427/238; 141/1, 4, 5, 51; 422/50, 57, 58, 61, 63, 64, 62, 73, 100, 101, 102, 71; 436/178, 180, 501, 527, 528, 529, 540, 805, 807, 808, 810, 43, 47, 513, 542, 545

[56] References Cited

U.S. PATENT DOCUMENTS

| | | | |
|---|---|---|---|
| 3,469,438 | 9/1969 | Gaumer | 73/53 |
| 3,684,448 | 6/1970 | Stricker | 23/230 B |
| 3,723,066 | 3/1973 | Moran | 23/253 R |
| 3,768,978 | 10/1973 | Grubb et al. | 422/100 |
| 3,826,621 | 7/1974 | Johnson, Jr. et al. | 436/180 |
| 3,846,077 | 11/1974 | Ohringer | 422/100 |
| 3,850,136 | 11/1974 | Ruzzo | 118/667 |
| 4,087,248 | 5/1978 | Miles | 23/230 B |
| 4,117,728 | 10/1978 | Johnson | 422/100 |
| 4,210,418 | 7/1980 | Brown et al. | 436/810 |
| 4,225,784 | 9/1980 | Barrett | 436/810 |
| 4,280,992 | 7/1981 | Sugiura et al. | 436/527 |

OTHER PUBLICATIONS

Rogers and Miles, "Automation of Radioimmunoassays," Radioimmunoassay, CRC Pres, Inc., pp. 127–145 (1981).

Primary Examiner—Michael S. Marcus
Attorney, Agent, or Firm—Townsend & Townsend

[57] ABSTRACT

Method and apparatus are provided for carrying out multiple simultaneous transfers of fluid. The method and apparatus are particularly directed toward immunoassays wherein immunologically active compounds, such as antigens and haptens, are detected through their associated antibodies. The device relies on the ability to transfer fluids, such as biological samples and reagents, between a reservoir and an associated receptacle. By providing a receptacle having a port at its lower end and which is otherwise hermetically sealed, such fluid transfer can be effected by immersing the port beneath the surface of the fluid in the reservoir and manipulating the pressure on the remaining surface area outside the port. The transfer of biological fluids at positive pressure provides enhanced fluids flow characteristics, particularly reduction or elimination of the tendency of these fluids to froth or bubble. Moreover, since the fluids can easily be manipulated, they can be agitated to speed up the reaction and reduce the overall reaction time and can be transferred from the reaction zone to allow interim measurements of the extent of reaction to provide for a rate mode assay. The method and apparatus also find use in preparing solid phase reagents for use in assay systems, as well as a highly accurate pipetting system in analytic applications not limited to immunoassays.

21 Claims, 9 Drawing Figures

METHOD AND APPARATUS FOR PERFORMING ASSAYS

BACKGROUND OF THE INVENTION

1. Field of the Invention

Use of immunoassays for the detection of physiological compounds of interest is now widespread. Immunological reactions offer specificity and sensitivity not available in other quantitative diagnostic methodology. Despite such inherent accuracy, immunoassays are subject to a wide variety of errors. Variations in temperature and reaction times can be critical. Systems requiring separation are highly sensitive to errors in the separation of "bound" and "free" labelled species (mis-classification error). Manipulative techniques, such as the preparation, measurement and transfer of reagents (pipetting errors) are invariably important. Sophisticated assay techniques using sequential and/or non-equilibrated reactions are especially vulnerable.

The quantitation of the compound of interest in an unknown sample is determined by comparing the observed result obtained with the unknown to the result obtained when assaying several solutions of varying known concentrations (standard solutions) to obtain a standard curve. It is therefore extremely important that all the assays (both standard and unknown) be carried out in the same way and with reagents of uniform characteristics. This requires the highly accurate and reproducible transfer of reagents in each of the unknown and standard assays. Moreover, in most immunoassay systems all reactions are terminated after a precise time interval by separating the "bound" from the "free" labelled species. In order to minimize errors, such termination is usually effected after the reactions are 70–90% complete and changing slowly with time.

There is a continuing need for a simple, accurate technique for carrying out assays, in particular immunoassays, where parameters such as reaction times, amounts transferred and reacted, and the like can be accurately controlled. Moreover, there is a need to be able to perform multiple simultaneous assays where deviations as to reaction time, amount transferred, and the like can be minimized among the various unknown and standard solutions. It is particularly desirable that such techniques be easily automated to carry out assays involving multiple, sequential addition and reaction of reagents.

One problem in achieving such a technique has been the nature of the fluid being analyzed. Biological fluids, such as blood, serum and saliva, are relatively viscous and contain a high protein concentration as well as large amounts of entrapped (dissolved) gases. The transfer of such fluids often causes release of the dissolved gases which in turn causes bubbling and frothing which can interfere with the assay.

Heretofore, the transfer of such fluids in automatic assay devices has been accomplished using negative pressure, typically using a syringe or a pipette bulb, to draw the sample fluid and/or reagents into a reaction or transfer receptacle. Such negative pressure aggravates the bubbling and frothing, which in turn prevents the accurate transfer of the fluids, and in some cases interferes with the progress of the desired reaction.

The inability to freely transfer biological fluids has other adverse consequences in performing automated assays. When carrying out assays in which one of the reactants is in the solid-phase, it would be desirable to periodically determine the progress of the reaction, both to investigate the kinetics of the reaction and to accurately predict the end-point of the reaction as early as possible. However, the need to completely separate the liquid and solid phase (which potentially causes frothing in the liquid phase) to measure the label, generally precludes such a technique. Moreover, the need to wash the solid phase to remove nonspecifically bound label during the course of the assay dilutes the assay medium and affects the accuracy of the assay.

It would also be desirable to continuously or periodically agitate the biological fluid in the assay medium to accelerate the progress of the reaction. Because of the slow rate of diffusion of the large molecules involved in solution, and the limited area of immobilized reagent, assays can take many hours to reach completion. While the assay time could be reduced by agitating the reagents, the frothing induced by agitation prevents accurate performance of the assay.

A final shortcoming of the prior art has been the difficulty in preparing suitable solid-phase reagents, a process which is often time-consuming and expensive. Solid-phase reagents typically comprise test tubes (or other vessels capable of holding liquid) in which a reagent has been deposited over a portion of the inner wall of the vessel. Alternatively, polystyrene balls, glass or polysaccharide beads, and the like may be provided to support reagent in the vessels. Regardless of the exact configuration of the solid phase, it is critical that the vessels be prepared under precisely controlled conditions so that the solid phase in each vessel has the same characteristics.

2. Description of the Prior Art

Automated systems for measuring a variety of samples may be found in U.S. Pat. Nos. 3,469,438; 3,684,448; 3,723,066; and 4,087,248. A listing and review of various automated radioimmunoassay systems are provided in an article by Rogers and Miles entitled "Automation of Radioimmunoassays", RADIOIMMUNOASSAY, CRC Press, Inc. pp. 127–145 (1981).

U.S. Pat. No. 4,087,248 discloses a particular solid phase reactant comprising a transfer pipette tip having the reactant bound to its innersurface. The tip is mounted on a syringe so that reactant solutions may be drawn up by creating a negative pressure in the tip.

SUMMARY OF THE INVENTION

A method and apparatus are provided for performing multiple, simultaneous transfers of fluid between a plurality of locations. The invention finds use in performing automated assays, in automated pipetting systems, in preparing solid phase reaction components, and in similar applications requiring highly accurate and reproducible transfer of fluid between at least two locations.

The invention finds particular use in performing immunoassays employing members of a pair of specifically bindable substances (SBS), one of which is in insolubilized form. The SBS pair includes a ligand and a receptor for the ligand. A receptor is any organic compound or composition which can differentiate, primarily by a significant difference in binding constant, its conjugate ligand from other compounds, particularly those compounds having a similar structure.

For the most part, ligands will be haptens and antigens, and receptors will be antibodies (antiligands) although other proteins and polysaccharides may also be employed as receptors. Where antibodies are employed with conjugate haptens or antigens, these compounds will be referred to as immunological bindable substances (IBS).

The apparatus employs one or more small receptacles having a single opening, but which are otherwise hermetically sealed. Usually, the receptacle comprises an elongate chamber having a relatively narrow port at one end. The narrow port permits fluid to be retained in the receptacle by surface tension and provides effective agitation as the fluid passes in and out, as described hereinbelow. The chamber may be cylindrical, conical or pyramidal, with the port typically being located at the apex of the conical and pyramidal structures.

The port usually comprises a tube, where the volume of the tube is very much less than the volume of the chamber. Thus, the volume of liquid in the tube can often be ignored when performing the analytic techniques of the present invention, as described hereinafter.

The receptacles are arranged within the apparatus so that the openings are disposed downward. One or more reservoirs are arranged adjacent the open end of one or more receptacles. Usually, the reservoirs are openended vessels having a volume corresponding to the volume of the receptacle. Under certain circumstances, as described hereinafter, the volume of the reservoir may be much greater than, or less than, the volume of the receptacle.

By immersing the port of a receptacle beneath the surface of a fluid in a reservoir, the fluid can be caused to enter the receptacle by elevating the pressure on the surface of the fluid outside the receptacle. The fluid will remain in the receptacle until the surrounding pressure is lowered. In this way, the fluid can be transferred back and forth between the receptacle and the reservoir, or between two or more reservoirs using the receptacle as a transfer vessel to carry fluid between the reservoirs. Since the fluids are transferred under positive pressure, the problems of the prior art resulting from the release of dissolved gases are largely avoided.

The apparatus finds particular use in performing immunoassays, where either the receptacle, the reservoir, or both will include one or more reaction zones having one member of an SBS, typically an IBS, immobilized therein. A sample may then be reacted with the immobilized SBS merely by manipulating the reservoirs relative to the receptacles, and manipulating the pressure in a predetermined manner to carry out the desired assay. More than one reaction zone can be employed to perform multiple assays within a single receptacle or single reservoir.

To perform multiple simultaneous assays, it is desirable that the apparatus include means for making simultaneous measurements at each of the reservoirs, each of the receptacles, or both the reservoirs and receptacles. Such measuring means should be capable of detecting the labelled species in a manner that relates to the amount of analyte in the sample. In the specific embodiment, a multiple-head gamma counter is described, but the method can be carried out with any other suitable detector, e.g. spectrophotometers, fluorescence detectors, magnetometers, and the like.

The use of positive pressure to effect transfer of the sample and/or reagents to the reaction zone has several advantages. First, the elevated pressure inhibits the release of dissolved gases from the sample and largely prevents bubbling and frothing of the sample fluids. Second, when running multiple assays in a single machine, the reservoirs can be located in a common plenum so that it is a simple matter to effect simultaneous fluid transfer between all of the reservoirs and receptacles. Third, the amount of fluid transferred to the receptacle can be controlled very accurately and uniformly since it depends only on the pressure level, which can be accurately controlled and is common to all reservoirs. Furthermore, slight deviations from the desired pressure will affect all receptacles, unknown and standards, alike so that potential errors are compensated. This is in contrast to mechanical systems, such as simultaneously actuated syringes, where variations in the amount transferred by a particular syringe introduce inaccuracies between the various standards and samples being assayed.

DESCRIPTION OF THE SPECIFIC EMBODIMENTS

The subject invention is concerned with carrying out assays, particularly immunoassays involving a pair of specifically bindable substances (SBS) including a ligand and a ligand-specific receptor. Receptacles having one opening are employed and the introduction and removal of reagents from one or more associated reservoirs is accomplished by immersing the opening of the receptacle beneath the surface of the fluid in the reservoir and manipulating the pressure on the surface of said fluid. The technique and apparatus of the present invention finds particular use in any type of assay wherein one of a specifically bindable substance pair (SBS), including haptens, antigens, antibodies, enzymes, enzyme substrates, serum proteins, tissue receptors, and the like, is insolubilized within either the receptacle, the reservoir, or both, typically on the inner wall of the receptacle. The invention is not limited, however, to such assays and binding reactions and can be applied to a wide variety of clinical techniques where the ability to carefully measure and transfer fluids between vessels is a requirement.

To carry out the assay, a reagent is typically provided which comprises a member of the SBS pair and is, therefore, able to bind to the insolubilized member. The reagent is modified in some manner so as to be capable of detection and measurement. Various atoms or compounds may be employed to provide a detectable signal, such as radioactive atoms, e.g. $^{125}I$, $^{3}H$, $^{14}C$, and the like; stable free-radicals; magnetic particles; enzymes; enzyme co-factors; fluorogenic substrates; bacteriophages; dyes; and chromophores. The reagent so modified will be referred to as the labelled reagent.

By providing for either a competition between the labelled reagent and the analyte for the immobilized member of the SBS pair (competitive binding technique), or by serially introducing the analyte followed by a labelled reagent capable of binding to the immobilized analyte in the receptacle (reagent excess or "sandwich" assay technique), the amount of analyte present in the sample will affect the amount of label which is insolubilized. Depending upon the nature of the assay, either the amount of label immobilized in the receptacle, or that present in the liquid phase, or both may be measured. The method and apparatus of the present invention are compatible with virtually any assay technique wherein one member of an SBS pair is immobilized to directly or indirectly bind the analyte of interest.

In its broadest form, the apparatus of the present invention includes a receptacle having a single opening, one or more reservoirs associated with the receptacle, and means for pressurizing fluid in the reservoir to cause the fluid to enter the receptacle. When adapted to perform immunoassays, the apparatus will typically also include means for isolating the reservoir from the major portion of the receptacle to prevent false detection of label, and means for detecting a labelled reagent in either the reservoir, the receptacle, or both. Each of these components of the present invention will be discussed in turn.

The receptacle can be composed of a wide variety of materials and need not be a single material. When used in performing assays, the material of the receptacle must be compatible with the particular label employed in the assay system. With fluorescent and enzymatic labels, it is necessary that the material allow light at the wavelength of interest to pass with minimal attenuation. A second important aspect of the receptacle is its internal surface or packing, either or both of which may provide a surface upon which a member of the SBS pair is insolubilized.

The materials of choice include a wide variety of polymeric materials, such as polyethylene, polypropylene, polyvinyl compounds, e.g. polyvinylchloride, polyacrylonitrile, polyacrylate, polymethacrylate, and copolymers thereof, polystyrene, nylon, polyterephthlate, cellulose, and the like. The group includes naturally occurring polymers, particularly modified naturally occurring polymers, and synthetic addition and condensation polymers. Also, inorganic substances, such as glass may be used.

Typically, only a portion of the innersurface of the receptacle or reservoir will be used for insolubilizing the member of the SBS pair. Alternatively, the reservoir may be adapted to retain small pellets, particles or beads of the above materials, which can serve independently or in conjunction with the innersurface of the receptacle as the area of insolubilization. As a second alternative, an uneven surface, e.g. projections, ridges, mounds or the like, can be provided on the inner surface of the receptacle to increase the area of the reaction zone.

Immobilization can be achieved by a wide variety of known techniques. Depending upon the nature of the particular surface, as well as on the nature of the particular SBS to be immobilized, physical absorption or adsorption may be employed.

Another technique is to covalently bond the member of the SBS pair to the inner surface. The surface can be activated or spacer arms can be covalently bonded to the surface by various techniques well known in the art, leaving a functionality which is either active or can be activated to react with the member of the SBS pair. For example, nitriles can be modified to form imido esters, which will react with the available amino groups on a antibody or antigen. There is an extensive literature concerning such bonding of proteins to surfaces employing activated carboxylic acids, carbodiimides, imido esters, active alkyl halides, etc., to form amido, amidine, or amino linkages.

Alternatively, an immunological spacer arm may be employed. This involves either binding or bonding a member of an IBS pair to the surface which then binds the complementary member of the IBS pair to the surface. In addition to using members of an IBS pair for binding, other materials may be employed including plasma binding proteins, tissue receptors, enzymes, cofactors, substrates, inhibitors and the like, that is, virtually any material which shows specificity for the analyte or for an intermediate reagent which shows such specificity.

The immobilized substance need not be a member of the SBS pair of interest. For example, immobilized avidin may act as the receptor in a multiple step assay wherein a biotinylated reagent, for example a biotinylated antibody to the analyte, is introduced in the second step. The binding of biotin to avidin will immobilize the antibody within the reaction zone and, for example, the assay may be completed by competitive binding between analyte, and a labelled analog of the analyte, to the biotinylated reagent. In this way, a single solid phase reagent (e.g., the avidin) may act as a "universal" receptor in performing a number of different solid-phase immunoassays.

Using any of these approaches, coating of the reaction zone may be conveniently accomplished in the receptacle of the present invention by manipulating the pressure on a reservoir to draw the particular member of the SBS pair into the receptacle to allow binding to the inner surface. After sufficient time, the coating solution is expelled from the receptacle and, if desired, the inner surface of the receptacle may be washed with appropriate media, usually a buffered solution of albumin or gelatin, to inhibit nonspecific binding during the assay. The immobilized SBS is usually an antibody or other receptor, but can be the analyte from the unknown sample.

The receptacles and/or reservoirs can be activated immediately prior to performance of the assay or may be prepared ahead of time and stored. Storage under relatively mild conditions is preferred, typically at a temperature in the range from about $-40°$ to $25°$ C., to inhibit the deactivation of the insolubilized material. Conveniently, the innersurface of the activated receptacles and reservoirs will be coated with liquid to maintain a moist polar environment. Illustrative materials include polyols, such as glycerol.

The structure of the receptacles may vary within wide limits. It is preferred that the receptacle include a hermetically sealed chamber having a single port defined by a relatively narrow tube. This structure has the advantage that it allows easy isolation of the receptacle chamber from the associated reservoir by inserting the tube through a small orifice in a shield, as described hereinafter. Typically, the chamber will have fixed walls and dimensions since fluid transfer to and from the chamber results from external manipulation of pressure on the fluid surrounding the port.

While the dimensions of receptacles may vary within wide limits, typically the reaction chamber will be generally cylindrical and have a diameter in the range from about 2 mm to 2 cm, more typically in the range from about 0.5 cm to 1 cm, and a volume in the range from approximately 0.1 to 20 ml, usually from about 0.5 to 5 ml. For use with optical detectors, opposing walls of the receptacle will be flat. The tube defining the port (referred to hereinafter as "entry tube") should have a volume which is much smaller than the volume of the reaction chamber and an inner diameter sufficiently small so that surface tension will prevent fluid from draining when the entry tube is withdrawn from the fluid in the reservoir. The tube diameter will typically be in the range from 0.25 mm to 3 mm, more usually in the range from 0.5 mm to 1.5 mm. The length of the entry tube will be determined by the overall dimensions of the assay machine; it must have a sufficient length to reach the associated reservoir(s) and to penetrate beneath the surface of the fluid therein, typically from about 0.5 cm to several centimeters.

The mechanical strength of the receptacle is not critical since the internal and external pressures will normally be balanced. With such pressure-balanced operation, it is necessary only that the receptacle wall have sufficient thickness so that it will retain its shape under the very small pressure differential, typically several inches of water as discussed hereinbelow.

Under certain circumstances, however, it may be desirable to mount the chamber of the receptacle outside the pressure-controlled plenum housing the reservoir. In that event, the receptacle will experience significant differential pressures, typically from 15 to 25 psi, and will have to be constructed to withstand such pressures.

Associated with each receptacle will be one or more fluid reservoirs intended to hold, for example, the samples containing the unknown(s), reagent solutions including the labelled member of the SBS pair, standard solutions containing a known amount of the analyte, wash solutions (if necessary) and the like. When preparing (i.e., converting a portion of the interior of the receptacle into an active solid-phase reagent) a large number of receptacles simultaneously, a common reservoir holding a relatively large volume of the activating reagent may be employed. A large number of receptacles may thus be prepared under virtually identical conditions, i.e., concentration of the reagent solution, reaction time, temperature, pressure and amount (height) of reagent transferred into the reaction chamber.

In contrast, when assaying individual samples, at least one reservoir will be provided for each receptacle. When performing a multiple step assay requiring the serial addition of samples (including standards) and common reagents having a uniform concentration in each assay, it will be possible to have both individual reservoirs and common reservoirs for the common reagents which are sequentially exposed to the receptacles. Such an assay will be described in more detail hereinafter with the exemplary multiple step assay.

In heterogeneous (two-phase) reagent assays it will be necessary to isolate the receptacles from the reservoirs so that the labelled reagents in either the solid phase or the liquid phase may be detected without interference from the label remaining in the other phase. Such isolation may be accomplished in a variety of ways depending, in part, on the type of label chosen. In the case of enzymatic, fluorescent and chemiluminescent labels, a sufficient distance separating the reaction zone from the reservoir might be sufficient. In the case of radioactive labels, a more substantial barrier may be desired to block the radiation from the detector without requiring an excess length of entry tubing. A shield for radioactive labels would typically be composed of high-Z elements such as tin or lead. Conveniently, the shield may also act as a physical support for the receptacle with the entry tube of the receptacle projecting through a small orifice in said shield.

To effect fluid transfer between the reservoir(s) and the receptacle, a means is provided for manipulating pressure on the fluid surface in the reservoir. Since the port of the receptacle is immersed beneath the surface of the fluid, and the remainder of the receptacle is hermetically sealed, fluid will rise until pressure of the gas trapped in the receptacle is equal to the pressure on the fluid surface outside the receptacle less the hydrostatic head of the liquid column. Thus, the volume of liquid in the receptacle (and the amount of solid phase reactant, if any, exposed to the liquid) is determined by the volume of trapped gas remaining in the receptacle. If all receptacles in the assay machine have identical dimensions, then the volume of liquid and height of liquid caused to enter each receptacle will be identical when the fluid surface in the associated reservoirs are subjected to the same pressure.

To expose the reservoirs to identical pressure, the reservoirs will typically be enclosed in a plenum which is connected to a pressurizing means, typically a pump. Pressurization may be achieved using pressurized air, or if desired, an inert gas such as nitrogen or helium. It is preferred that the outside of the receptacle also be subjected to pressure to avoid stressing the receptacle. This is conveniently accomplished by enclosing the receptacles within the same plenum as the reservoirs. Alternatively, it may be desired to leave the receptacles outside of the pressure-controlled plenum. In that case only the entry tubes would penetrate to allow fluid to enter the receptacle when the pressure is elevated.

Aside from mechanical simplicity and inherent accuracy, the present invention provides a technique for reducing the time required for performing many assays. In an immunoassay where one member of the SBS is immobilized within a reaction vessel, reaction times can be quite lengthy because of the time required for the relatively large molecules involved to approach and specifically bind to the immobilized SBS. While it would be desirable to agitate the reactants to accelerate the speed of reaction, such agitation is interdicted by the proclivity of such fluids to bubble and froth when agitated.

It has been found, however, that such frothing is greatly diminished, and in many cases eliminated entirely, when the agitation is carried out under positive pressure. Thus, the present invention provides that the reactants may be agitated within the reaction zone by periodically varying the positive pressure on the fluid in the reservoir. Particularly where the SBS is bound to the wall of the reactant vessel, the reactant solution is able to move up and down the activated region to accelerate the reaction. Agitation in both the receptacle and reservoir is achieved as the fluid passes through the relatively narrow entry port. Such ability to agitate reactants under positive pressure is an advantage even in systems which do not include a solid-phase reagent.

The ability to freely transfer reactants between the reservoir and the receptacle affords a particularly sensitive assay technique for amplifying very low concentrations of analyte in a sample fluid. By locating a reaction zone having a limited amount of solid-phase reactant in the receptacle, a large volume of sample (containing a very low concentration of analyte) may be incrementally introduced by repeatedly introducing fresh aliquots of the large sample volume into the reaction zone. Over time, virtually all of the sample will be exposed to the reaction zone and most of the analyte will have had a chance to react. Such periodic transfer between the reservoir and reaction zone both agitates the sample to decrease the reaction time and localizes the detection signal corresponding to a given analyte concentration to intensify the signal. The theory underlying this technique is described in Miles, "Immunoradiometric Assay—New Developments in Theory and Practice", PROTIDES OF THE BIOLOGICAL FLUIDS, Peters (Ed.) Pergamon Press, Oxford, Vol. 24, pp. 695-704 (1976).

In a related technique, a biological sample containing high concentrations of non-specific proteins, such as albumin in blood plasma, may be initially diluted to prevent interference with the immunological reaction. Although the analyte has also been diluted, it can then be concentrated in the manner just described.

An additional advantage of the present invention is the reduced requirement for washing the reaction surface between successive steps of a multiple step assay. When two-phase assays are carried out by usual techniques, it is preferable to wash the solid phase between the various reaction steps in order to remove unbound reactants which would otherwise adhere to the solid surface after separation. The presence of a labelled species which has not participated in a specific binding reaction will result in inaccuracies. Moreover, the provision of a washing step in an automated assay system is mechanically complex, and the removal of reacting species by washing can itself be a source of error.

It has been found that when the phases are separated by reducing the positive pressure on the liquid phase to allow the liquid phase to drain from the receptacle, a very clean separation is achieved. That is, very little unbound reactant remains on the reaction surface. Thus, the need to wash the reactant surface between successive reaction steps is reduced or eliminated entirely.

The present invention is uniquely adapted to performing dynamic or rate mode assays where the extent of reaction between members of the SBS pair may be determined over the course of time. Heretofore, heterogeneous (two-phase) immunoassays have been performed by allowing the solid and liquid phase reactants to react for a predetermined amount of time prior to separation and detection. A dynamic heterogeneous assay has been prevented by the inability to periodically separate the phases prior to detection. So long as the two phases containing the label remain unseparated, it is impossible to determine the extent of the reaction.

While it would seem possible in theory to periodically separate the phases in order to obtain an interim measurement, this has been extremely difficult for several reasons. First, the bubbling of the sample fluid would only be worsened by repeated separation. Second, the need to wash the solid phase to obtain an accurate measurement of the label present (or to remove all unreacted label so that it can be measured in the liquid phase) is difficult and will increase the volume of the liquid phase having an adverse effect on the determination. Furthermore, there is no effective and simple way of separating and then reintroducing the solution to the solid phase. Such difficulties have effectively precluded clinical application of rate mode heterogeneous assays.

With the present invention, however, the problems of frothing and the necessity of washing are substantially eliminated and a rate mode heterogeneous assay becomes readily achievable. For example, the reaction may proceed in the receptacle (having the reaction zone) for a predetermined amount of time, after which the liquid phase is released back to the reservoir to terminate the reaction. The label may then be detected in either the reaction zone or the reservoir, as dictated by the particular assay involved, and the results may be recorded. By again elevating the pressure the liquid phase is returned to the reaction zone and the reaction may continue. Similarly, the reaction may be located in the reservoir and the detection step take place when the liquid phase is in the receptacle.

Such rate mode assays are particularly useful in identifying abnormal assay profiles resulting from protein interference, reagent irregularities, equipment malfunction, and the like. For example, it has recently been discovered that in reagent excess immunoassays, very high analyte concentrations sometimes result in a decreased (rather than increased) amount of bound label. By performing a rate mode assay, these abnormal samples may be identified, and erroneous results avoided.

In addition to providing a support for solid phase reactants, the receptacles can be used to take an aliquot of an unknown or standard solution and mix it with various diluents and reagents in a reservoir before beginning the reaction with a solid-phase reactant located either in a reservoir or in the receptacle itself. The solid phase reaction can include repetitive additions, separations and measurements, involving sequential reactions and washing steps, with several other reservoirs and solutions being involved. Because each unknown and standard solution is sampled and assayed by means of its own individual receptacle, no sample can interfere with the assay of another sample by contamination. Moreover, blockage in one receptacle will affect only one determination, and the remaining assays can be successfully completed.

More generally, this fluid transfer system can be used to take repeated samples of any type of homogeneous or non-homogeneous reaction system for the purpose of destructive or non-destructive testing, or further processing.

In addition to performing immunoassays, the apparatus of the present invention finds use in activating the receptacles and reservoirs by insolubilizing one of the members of an SBS pair therein. While a wide variety of substrates may be activated, such as pellets, beads, disks, and the like, the present invention finds particular use in insolubilizing a reactant on the inner wall of the receptacle. Typically, this will be accomplished by first deactivating a portion of the wall with an inactive species. This is easily accomplished by immersing the open end of a plurality of receptables into a common reservoir containing the deactivating reagent. A predetermined area of the inner surface of each of the receptacles may then be deactivated by raising the pressure in the plenum by a amount sufficient to raise the level of the deactivating reagent to desired height. After releasing the deactivating reagent back into the reservoir, or to a common drain, a second reservoir holding the desired member of the SBS pair may be brought into place. Then, by elevating the pressure above that used for the deactivating reagent, the active reagent will contact the inner surface of the receptacle to a desired height above the inactivated level. Thus, the area of the reaction surface or zone may be very accurately controlled both in the absolute sense that the desired area is achieved and in the relative sense that, even if small inaccuracies occur, a large number of receptacles will have been prepared under virtually identical conditions. Moreover, the operation is easily and economically performed by merely controlling the pressure in a closed vessel.

While the invention is primarily directed toward multiple simultaneous assays, the subject method also finds use for single assays. By using a single receptacle, an assay can be rapidly performed by the introduction and transfer of reagents between a multiplicity of reagent reservoirs by means of a receptacle. The advantages of reduced frothing, reduced assay time, elimination of washing, and precisely controlled preparation of the insolubilized reaction zone, apply to single determinations equally, as well as to multiple determinations, and can be achieved by no known prior method.

Figure 1A:
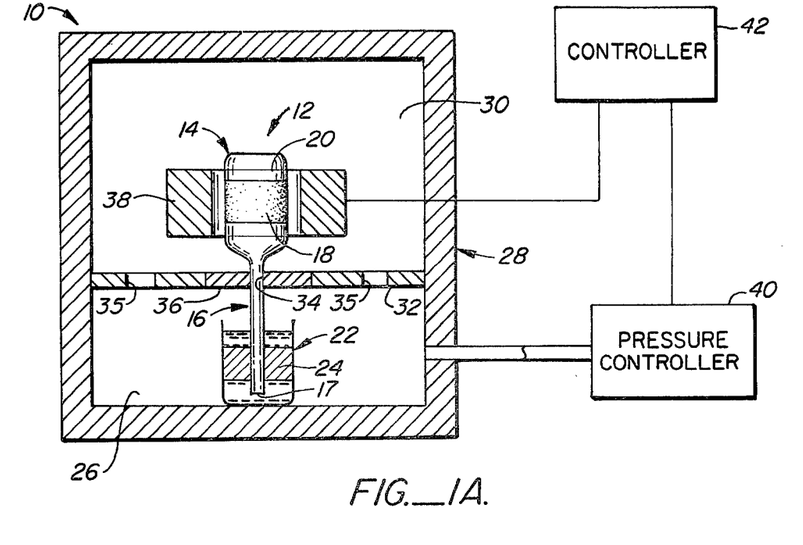
FIGS. 1A and 1B are schematic representations of the apparatus of the present invention including a single receptacle and a single reservoir.
Figure 1B:
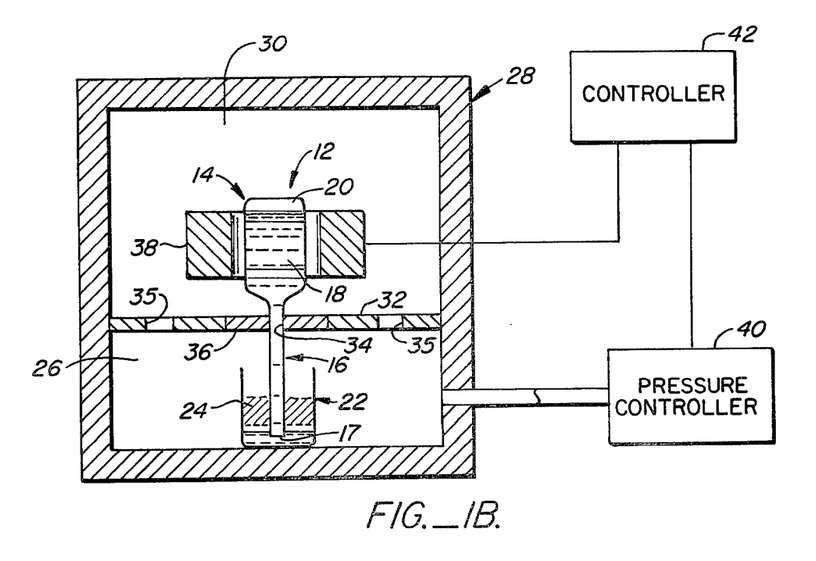

Referring now to FIGS. 1A and 1B, an assay machine 10 for performing a single assay using the method of the present invention includes a receptacle 12 having an upper chamber 14 and an inlet tube 16 which defines a port 17 at its lower end. Typically, the upper chamber 14 will include a reaction zone 18 comprising an immobilized member of an SBS pair, as described hereinbefore. The reaction zone 18 will usually occupy the major portion of the inner wall of chamber 14 and may include an uneven surface for increasing the area of the solid phase reactant. A head space 20 will remain above the reaction zone 18 to allow a volume in which the internal gases compress as the liquid is driven upward into the receptacle 12. As described hereinbefore, the minimum volume of the head space 20 relates directly to the pressure required to drive the fluid fully upward into the reaction zone 18. Typically, the volume of the head space 20 will be chosen so that a pressure in the range from 15 to 25 psig will accomplish complete filling of the reaction zone 18.

Associated with the receptacle 12 is a reservoir 22 having an opening directed upward which is large enough to receive the inlet tube 16. The shape of the reservoir is not critical with the only requirement being that the reservoir be able to hold liquid under gravity.

The reservoir 22 may also include a reaction zone 24. Depending on the particular assay performed, the reaction zone 24 may have characteristics similar to or different from the reaction zone 18 in the receptacle 12. Usually, the reaction zone 24 will comprise an immobilized member of an SBS pair which is specific to a different species from the reaction zone 18. In that way, a different species will be selectively bound depending on whether the sample is present in either the receptacle 12 or the reservoir 22.

Typically, the assay device of the present invention will include means for manipulating the receptacle 12 relative to the reservoir 22 so that a single receptacle may interact with more than one reservoir, and a single reservoir may interact with more than one receptacle. As illustrated in FIGS. 1A and 1B, however, the receptacle 12 is fixed relative to the reservoir 22 with its port 17 disposed relatively near the bottom of the reservoir. Such construction is adequate to carry out single step assays where the necessary reagents are mixed prior to being introduced to the reservoir.

The volume of the reservoir 22 will typically be at least as large as the volume of the receptacle 12 less the volume of the head space 20. The volume can exceed the receptacle volume by manyfold, particularly when it is desired to perform a "concentrating" assay, as described hereinbefore, where portions of sample are periodically transferred into the reaction zone 18 to increase the amount of analyte exposed to the reaction zone.

The reservoir 22 is located in a plenum 26 defined by an enclosure 28 as illustrated in FIGS. 1A and 1B. The enclosure 28 also includes an upper plenum 30 enclosing the upper chamber 14 of the receptacle 12.

The upper and lower plenums 26,30 are separated by a partition 32. Conveniently, the receptacle 12 is supported on the partition 32 with inlet tube 16 projecting downward through an orifice 34 formed in the wall. As illustrated, a portion of the partition 32 which lies between the upper chamber 14 and the reservoir 22 defines a shield 36 to isolate the labelled species during the detection step of an assay, as described hereinafter. The shield 36, of course, need not be part of the partition 32 and could be separately supported at any point between the chamber 14 and the reservoir 22. It is important only that the area of the shield 36 be sufficient to isolate a detector associated with reaction zone 18 from free (non-bound) label in the reservoir 22, or reaction zone 24 from free label in the receptacle 12.

The diameter of the orifice 34 will typically be equal to the outer diameter of the inlet tube 16 so that the partition 32 directly supports the receptacles. Holes 35 are provided in the partition 32 to allow pressure in plenums 26 and 30 to equilibrate as the pressure is varied to effect changes in the liquid level in the receptacle 12.

It is desirable that the pressure in the upper plenum 30 closely match the internal pressure in the upper chamber 14 so that excessive stress is not placed on the chamber material. By equilibrating the pressure internal to chamber 14 with that on the surface of the fluid in the reservoir 22, the difference between the external and internal pressure on the upper chamber 14 is limited to the hydrostatic head of the liquid column in the receptacle 12, typically less than several inches of water. This pressure differential is negligible and the receptacle 12 may be formed from relatively fragile materials, such as very thin glass or plastic, as described hereinbefore.

Of course, it is possible to operate the apparatus by sealing the plenum 26 and leaving the environment surrounding the upper chamber 14 at ambient pressure. By then pressurizing the plenum 26 to elevate the liquid within the receptacle 12, the chamber 14 will experience a pressure differential between its interior and exterior equal to the elevated pressure in the plenum 26. In that case, it would be necessary to construct a stronger receptacle 12 capable of withstanding such a differential pressure without breaking, typically a pressure differential of from 15 to 25 psig maximum.

A detector 38 is located adjacent the reaction zone 18 in the upper chamber 14. The type of detector will depend on the particular label to be detected. For example, an assay which employs radioactive label will use a gamma counter for detecting the presence of the label in the upper chamber 14. Similarly, a fluorometer will be employed for a fluorescent label, and a spectrophotometer will typically be employed for an enzymatic label. In any case, the detector 38 is capable of detecting all label located in the upper chamber 14, typically label bound within the reaction zone 18, at various times during the assay. As stated hereinbefore, the detector 38 will be isolated from any label present in the reservoir 22 by the shield 36.

Although not illustrated, a similar detector may be present adjacent the lower reaction zone 24 associated with the reservoir 22. This second detector would be capable of detecting label present in the reservoir 22 typically label bound in the reaction zone 24. It will be appreciated by those skilled in the art, that various assays may be performed where the separation of the bound from the free species could take place in either the chamber 14, the reservoir 22, or both. Thus, whether detection occurs when the label is bound within the receptacle reaction zone 18, or within the reservoir reaction zone 24, is largely a matter of convenience. Moreover, the label detected may comprise the free label present in the sample solution after a portion of the label has been bound within either reaction zone.

A pressure controller 40 is provided to vary the pressure within the plenum 26 and usually also within the plenum 30. The pressure controller 40 may take a wide variety of forms such as a variable piston which compresses the gas within the plenum 26 by reducing its volume. Typically, however, the pressure controller 40 will be a pump operating in conjunction with a pressure relief means, or gas recirculation system, to maintain a desired pressure within the plenums 26 and 30.

A programmable controller 42, typically a microprocessor, although it could be a conventional drum-type controller, is provided to vary the pressure induced by the pressure controller 40 according to a preselected pattern. The pattern, of course, will be selected to transfer fluid between the reservoir 22 and the chamber 14 according to a desired schedule.

In addition to controlling the pressure controller 40, the controller 42 will include means for recording the output of the detector 38. Such means may comprise a chart recorder suitably adapted to process the output signal of the detector 38. Alternatively, when the controller 42 is a microprocessor, the means may comprise an analog-to-digital converter which conditions the signal from the detector 38 for storing in memory associated with the microprocessor. Such recording means are well known and will not be discussed further.

FIG. 1A illustrates the assay machine 10 in its unpressurized state with the liquid present substantially in the reservoir 22. By elevating the pressure in plenum 26, the pressure on the liquid increases, overcoming the pressure in the receptacle 12, and driving the liquid upward. By fully elevating the pressure to a preselected level depending on the ratio of head space 20 volume to total receptacle 12 volume, the liquid is driven fully into reaction zone 18, as illustrated in FIG. 1B.

While the single assay machine 10 just described will provide the benefits associated with the present invention, it will most often be desirable to provide a multiple assay machine which allows the performance of multiple simultaneous assays. In general, such a multiple assay machine will include a plurality of reservoirs associated with each of a multiplicity of receptacles. The reservoirs will be located in a common plenum having means for controlling the pressure therein so that fluid may be caused to enter each of the receptacles simultaneously from associated reservoirs. In addition, means for manipulating the various reservoirs relative to the receptacles will be provided so that multiple step assays involving separate reagents may be performed without the necessity of manually changing the reagent in the reservoir during the assay.

Referring now to FIGS. 2 and 3A–3C, a multiple assay machine 50 comprises an enclosure 52 having a partition 54 which supports a plurality of receptacles 56. A carousel 58 mounted within the enclosure 52 carries a plurality of reservoirs 60. An actuator 62 is provided for manipulating the carousel 58 so that various of the reservoirs 60 may be brought into fluid communication with the receptacles 56, as described hereinafter. A multiple-head detector 64, a pressure controller 66 and a controller 68 complete the necessary components which comprise the multiple assay machine 50.

Figure 2:
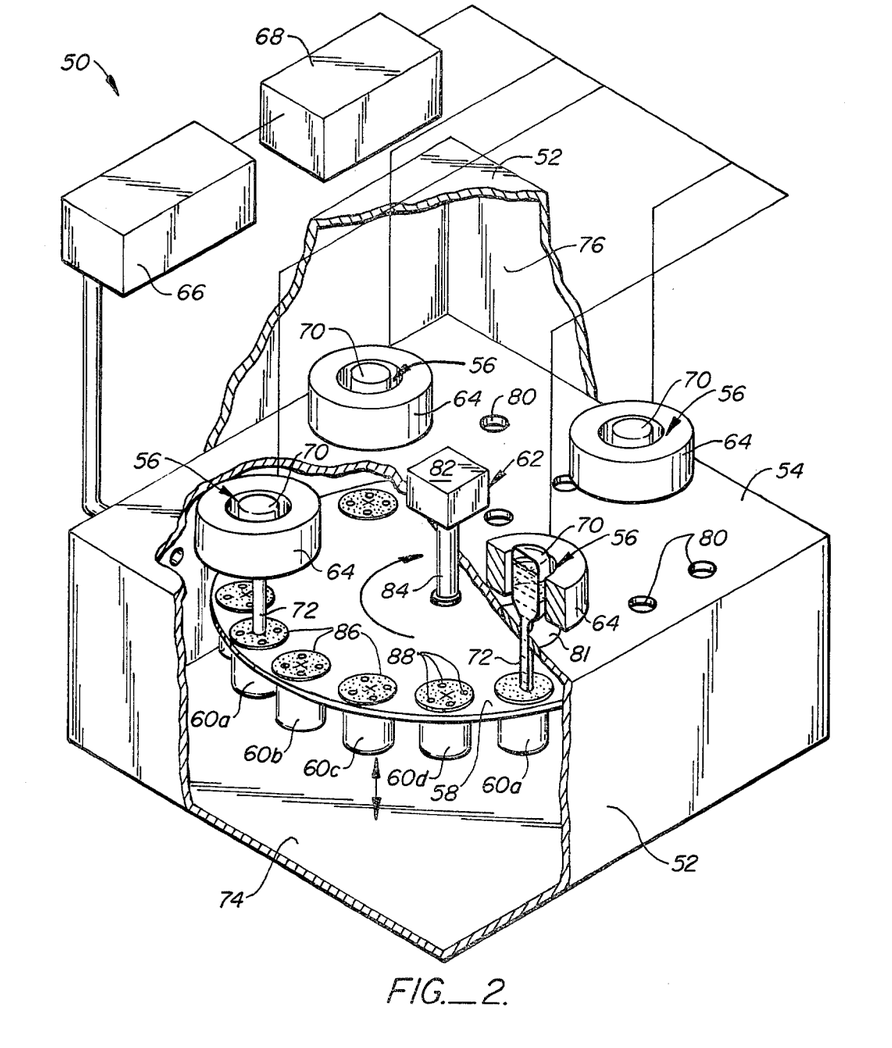
FIG. 2 is a schematic representation of the apparatus of the present invention including multiple receptacles and reservoirs.

The specifications of the receptacles 56 and the reservoirs 60 are as described hereinbefore. Each receptacle 56 includes an upper chamber 70 and an inlet tube 72 which projects downward into the vicinity of the reservoirs 60.

The enclosure 52 includes a lower plenum 74 which receives the reservoirs 60, and an upper plenum 76 which receives the upper chambers 70 of the receptacles 56. As was the case the with the single assay machine 10, the plenums 74 and 76 are typically in fluid communication (defined by holes 80 in partition 54) so that the pressure in each is equilibrated. Usually, a portion of the partition 54 adjacent each of the receptacles 56 will define a shield 81 to isolate the multiple head detector 64.

The particular specifications of the multiple head detector 64 will, of course, depend on the nature of the label to be detected. In general, however, it is desirable that the multiple head detector be compact so that its physical placement within the assay machine 50 is straightforward and interferes little in the operation of the device. One such assay machine is described in the patent application of Rogers et al., U.S. Ser. No. 33,629 filed on Dec. 22, 1981, the disclosure of which is incorporated herein by reference.

In FIGS. 2 and 3A–3C, the detector heads 64 are illustrated adjacent the upper chamber 70 of the receptacles 56. This placement is preferred in the embodiment illustrated since the receptacles 56 remain stationary while the reservoirs 60 are manipulated by the actuator 62. An alternate embodiment, however, might employ multiple receptacles 56 in conjunction with one or more fixed reservoirs wherein it would be easier to associate the multiple head detector with the stationary reservoirs. Of course, it would be possible to mount the detector heads 64 on the carousel 58 so that they move therewith. This might be necessary particularly when it is desired to detect label when present both in the receptacles and in the reservoirs. The wide variety of constructions which may be desired in particular circumstances makes it impossible to list such constructions exhaustively. It is pointed out only that the present invention is applicable to a wide variety of embodiments and is not limited to the particular embodiment illustrated.

The actuator 62 comprises a motor 82 and a shaft 84 projecting downward therefrom. The carousel 58 is mounted at the lower end of the shaft 84, and the motor 82 may be driven both to rotate the shaft and to reciprocate the shaft upward and downward. In this way, the various reservoirs 60 may be serially brought into contact with the inlet tubes 72 of the receptacles 56.

Of course, a wide variety of mechanisms may be employed for manipulating the reservoirs 60 relative to the receptacles 56. For example, the reservoirs might be mounted on a plate capable of motion along each of the three rectangular coordinates. Such a construction would be preferred when a particularly compact construction is required since a high density of reservoirs can be mounted on the plate. The actuator for manipulating the plate would be more complex, although well within the state of the art. Other mechanisms for manipulating the reservoirs, the receptacles, or both, will occur to those skilled in the art and the present invention is not limited to any particular mechanism.

In the particular embodiment illustrated, there are four reservoirs 60a, 60b, 60c and 60d associated with each receptacle 56. The additional reservoirs are used to provide additional reagents necessary for a multiple step assay, as described in the Experimental Results.

Figure 3A:
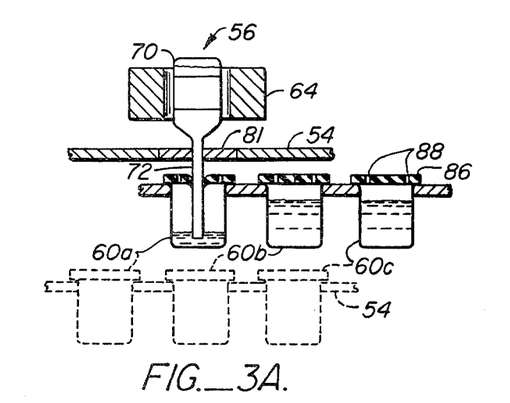
FIGS. 3A, 3B and 3C illustrate the performance of a multiple step assay.
Figure 3B:
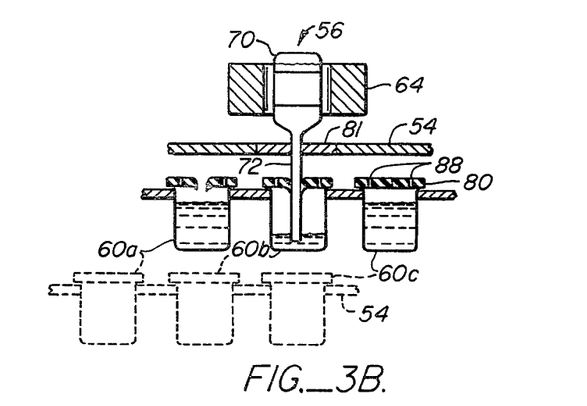
Figure 3C:
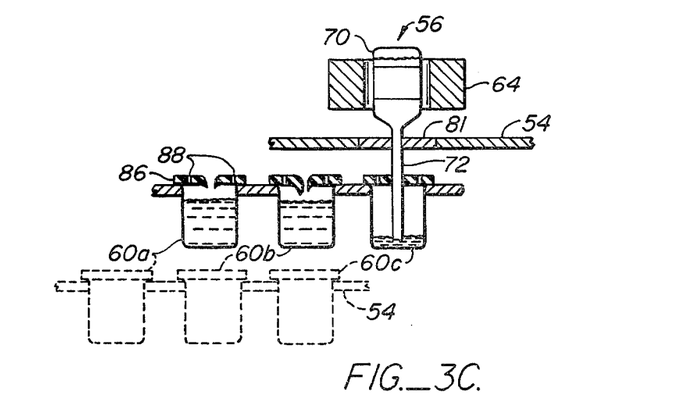

The various samples and reagents involved in the particular assay will typically be prepared and loaded into the reservoirs 60 prior to placing the reservoirs in the enclosure 52. The reservoirs 60 are then loaded onto the carousel 58 and the carousel is brought into the appropriate position relative to the receptacle 56 with the inlet tube 72 of each receptacle projecting downward into the first reservoir 60a (FIGS. 2 and 3A). After the necessary reaction, aspiration or incubation involving the reagent in the first reservoir 60a has been completed, the carousel 58 will be lowered and incrementally rotated until the second reservoir 60b is properly aligned with the entry tube 72. The carousel is then raised, immersing the entry tube 72 beneath the surface of the fluid in the second reservoir 60b (FIG. 3B). Similar incrementing is provided to properly position the third reservoir 60c (FIG. 3C) and the fourth reservoir 60d.

Although not illustrated, a mechanism for delivering samples, reagents and the like to the reservoirs may be provided so that the reservoirs do not have to be removed from the assay machine 50. The structure of such a mechanism would depend on many factors, including the number of reservoirs associated with each receptacle, the nature of the actuator for manipulating the reservoirs, etc. The present invention is not limited to the provision of such a mechanism, much less to the particular structure of such a mechanism.

A blotter 86 may be provided over the opening of each reservoir 60 to clean the outer surface of the inlet tube 72 before or after introduction into the reservoir. The blotter 86 will typically be formed from a wicking material and substantially cover the opening of the associated reservoir 60 so that the entry tube 72 will be wiped as it penetrates the blotter. Holes 88 must be provided in the blotters 86 to equalize the pressure in the enclosure 52 with that over the surface of the fluid in the reservoir 60.

The remaining systems of the multiple assay machine 50 are similar to those already described in connection with the single assay machine 10. The pressure controller 66, typically a pump, is provided to pressurize the interior of the enclosure 52. If it is desired to pressurize the enclosure with an inert gas, such as helium, a purge and recycling system (not shown) may be provided in connection with the pressure controller 66. A controller 68 is provided to coordinate and record the various functions of the multiple assay machine 50. Specifically, the controller 68 will manipulate the actuator 62 in the proper sequence and with the proper timing to carry out the desired assay, control the pressure controller 66 to properly coordinate the manipulation of the fluid level in the various receptacles 56, and communicate with the detectors 64 to record the output as desired.

EXPERIMENTAL RESULTS

As further illustration of the subject invention, the performance of three exemplary assays utilizing the assay machine of the present invention will be described. The assay machine was generally of the type illustrated in FIGS. 1A and 1B, except that it included provisions for holding up to six receptacles and reservoirs simultaneously. Reagents were changed by manually filling the reservoirs at the appropriate point in the assay. The receptacles employed in each of the experiments were formed from polypropylene having a chamber volume of 1.5 ml and an inlet tube (port) diameter of 1.0 mm.

These examples are for illustration only and not intended to define the limits of the invention.

A. Thyroxine (T4) Radioimmunoassay Using Competitive Binding Technique

1. Activating the Receptacles

Three of the receptacles described hereinabove were placed in the assay machine at ambient pressure and temperature with their inlet tubes below the surface of a common reservoir containing a 1:2000 dilution of rabbit anti-T4 serum in a solution of sodium bicarbonate (0.2 M, pH9.0). The reservoir was then pressurized to 18 psi so that approximately 900 $\mu$l of the solution entered the receptacles. After 5 minutes, the fluid in the receptacles was expelled to the reservoirs by briefly returning the pressure to ambient. The pressurization and depressurization cycle was repeated every five minutes for a total duration of 30 minutes, resulting in physical adsorption of some of the anti-T4 onto the interior of the receptacles. The antibody solution was then replaced by a wash solution of phosphate buffer (0.05M, pH8.0) containing 0.1 g/100 ml bovine serum albumin, 0.45 g/100 ml NaCl, and 0.01 g/100 ml sodium azide, referred to hereinafter as BSA-buffer. The reservoir containing the BSA-buffer was then pressurized and depressurized five times with a cycle time of 30 seconds in order to wash the interior of the receptacles free of any loosely bound antibody and coat any unreacted surface within the reaction zone to prevent non-specific binding.

2. Assay

Three reservoirs were manually filled with 50 $\mu$l of human sera containing thyroxine concentrates of 0, 4 and 20 $\mu$g/100 ml, respectively, in 1.15 ml of Tris buffered saline with 0.02 M sodium azide, 0.4 mM ANS, 0.6 mM sodium salicylate and about 120,000 dpm (disintegrations per minute) of $^{125}$I-labelled thyroxine, and placed in the assay machine. The total volume of solution in the reservoirs was 1.2 ml and the total amount of radioactivity was about 25,000 counts per two minutes. The background radioactivity measured in the presence of the receptacle alone was about 300 counts per two minutes. These reagents were obtained from a commercial T4 assay kit (Clinical Assays Corporation, Cat. No. Ca-535).

An activated receptacle was placed in each reservoir and the reservoirs were pressurized to 18 psi for five minutes in order to drive about 900 $\mu$l of the solution into the receptacle and cover the surface of the activated solid phase. The pressure was released back to atmospheric and the solution allowed to drain away from the activated solid phase. The radioactivity bound to the interior of the receptacle was then measured for two minutes, before again repressurizing the reservoir to reintroduce the solution into the receptacle. The cycle was repeated every five minutes (i.e., pressurized for three minutes and measure for two minutes) for a total of ten measurements after 50 minutes.

3. Results

Figure 4:
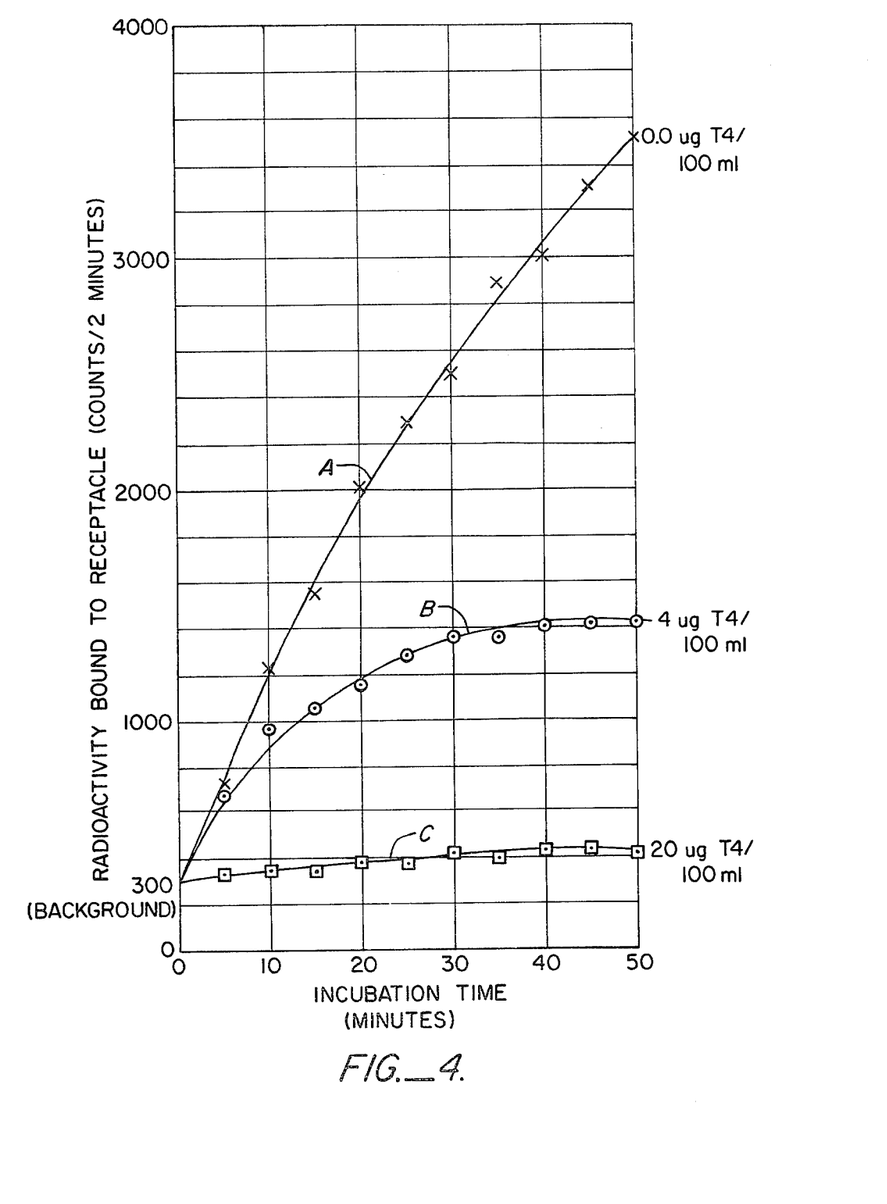
FIGS. 4, 5 and 6 are graphs illustrating the Experimental Results.

Referring to FIG. 4, the amounts of radioactivity bound to the reactive solid phases of the three individual receptacles are plotted against time. The slopes of these lines, as well as the predicted end-points, are inversely related to the amounts of non-radioactive T4 in the sample solutions. Curve A shows the rapid increase with time of the amount of radioactive T4 bound to the solid-phase in the presence of 50 μl of human serum containing no detectable non-radioactive T4. Curves B and C show the decrease in bound radioactivity when the human serum contained, respectively, 4 μg/100 ml and 20 μg/100 ml of added non-radioactive thyroxine.

The results demonstrate the feasibility of a rate mode or dynamic assay using the present invention, revealing the expected increase in bound radioactivity with time for the samples. Specifically, the observed separation between the three curves indicates that unbound radioactive label was expelled from the receptacle without the necessity of washing the reaction zone.

B. Hepatitis B Antigen Assay Using 2-Site Immunoradiometric Assay (2-Site IRMA) and Showing the Effect of Mixing 1. Activating the Receptacle Six receptacles were activated with a 1:500 dilution of a monoclonal anti-Hepatitis immunoglobulin (Centocor Corporation) in sodium bicarbonate, using a technique identical to that described in Example A.

2. Assay Reaction One

Six reservoirs were filled with human serum (1.2 ml, 1:10,000 BSA-buffer, Example A) containing identical concentrations of the hepatitis B antigen. Three of the reservoirs were placed in the assay machine each with an activated receptacle. The assay machine was pressurized to 18 psig in order to react the solutions with the solid-phase antibody in each receptacle. One receptacle was removed after 30 minutes, a second after 6 hours and the third after 24 hours. The serum was not agitated during preparation of the first of the receptacles.

The remaining three receptacles were also exposed for 30 minutes, 6 hours and 24 hours, respectively, during which time the assay machine was depressurized and repressurized every 10 minutes so that the solution drained out of each receptacle to effect agitation.

The receptacles were drained and washed with BSA-buffer (Example A) before proceeding with Assay Reaction Two.

3. Assay Reaction Two

After Reaction One had been terminated, the solutions of diluted human sera were manually replaced in the reservoirs by solutions containing approximately 120,000 dpm of an $^{125}$I-labelled monoclonal antibody to hepatitis B antigen having an approximate specific activity of 8 to 14 μC/μg. The reservoirs were then pressurized to 18 psi to drive this new solution into the receptacles and allow it to react with any hepatitis antigen bound to the solid-phase reactant. After 10 minutes the pressure was released and the solution drained away from the activated solid phase. The radioactivity remaining bound to the interior of the receptacle was then measured for two minutes, before again repressurizing the reservoir to continue the reaction of the solution with the solid-phase. Measurements were taken every 12 minutes for a total of 24 hours.

4. Results

Figure 5:
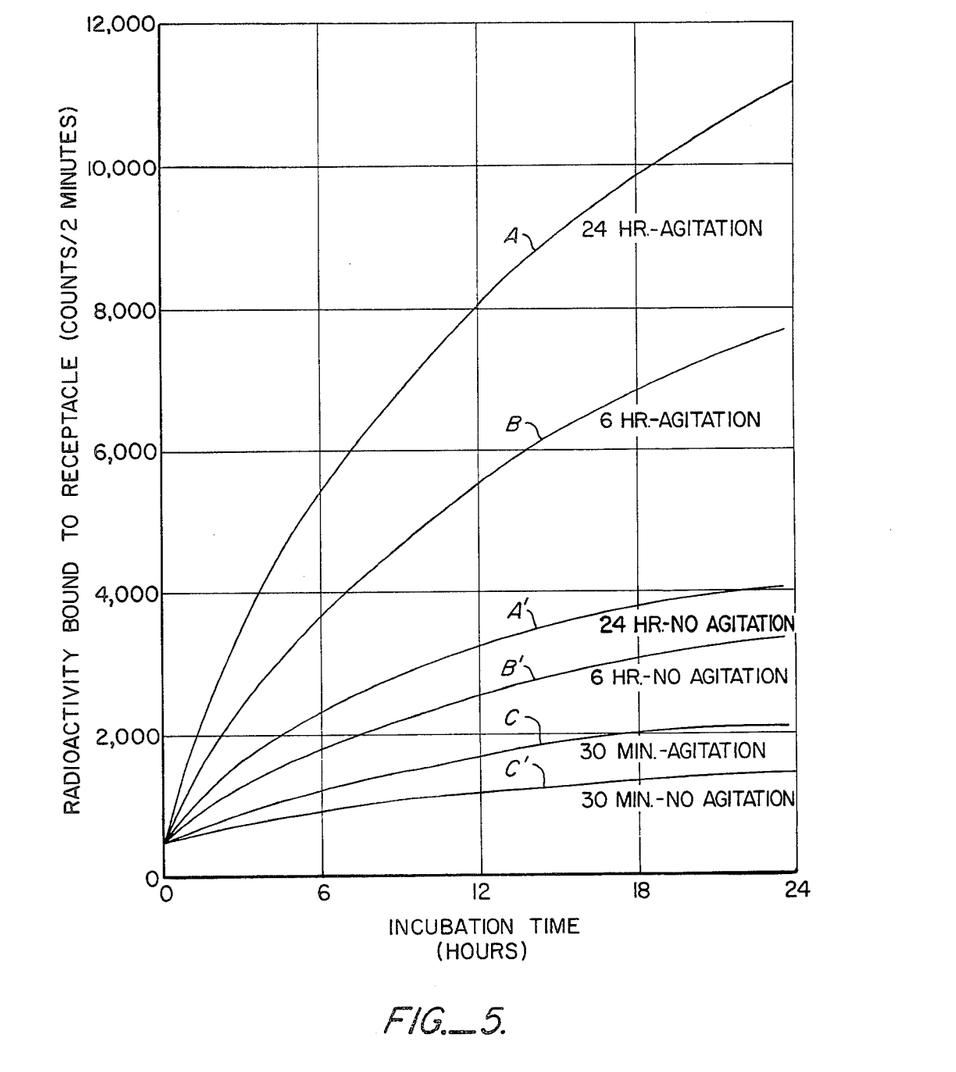

Referring to FIG. 5, the curves show the successive increase with time in the amount of radioactivity bound to the receptacle during Reaction Two, in the presence of the previously insolubilized hepatitis B antigen. Curves A, B and C represent the assays where Reaction One was performed with agitation, while curves A', B' and C' represent the assay carried out over the same duration, but without agitation. The total amount of radioactivity was about 24,000 counts per two minutes.

The amplitude of the dose response (at all time points) increased markedly as the duration of Reaction One increased. Moreover, there was a dramatic increase in the amplitude when Reaction One was carried out with repeated agitation, so that the amplitude of curve B (6 hours with mixing) was approximately twice that of Curve A' (24 hours without mixing). This indicates that rate of binding of the hepatitis antigen to the immobilized antibody was significantly increased when the liquid phase was periodically agitated. Thus, the present invention provides a method for significantly decreasing the time required to perform standard assays by decreasing the time required to approach equilibrium.

C. Two-site IRMA for IgE Using Single Incubation

1. Activating the Receptacle

The receptacle was activated with a fluorescent-labeled monoclonal anti-IgE immunoglobulin preparation, bound to the wall by reaction with an antibody directed against the fluorescent group. Both of these reagents were provided by Hybritech Incorporated. The non-fluorescent antibody was bound to the wall of the receptacle using the technique of Example A.

2. Assay

Because the solid-phase anti-IgE and reagent anti-IgE are directed to distinctly different sites on the IgE molecule, the assay reaction can be carried out in a single incubation. The reaction mixture contained 50 μl of a standard solution of IgE in human serum, 200 μl (about 25,000 counts per two minutes) of $^{125}$I-labeled anti-IgE and 1000 μl of BSA-buffer. Except for the BSA-buffer, all of these reagents are part of a commercial Tandem ® IgE assay kit (Cat. #3053, Lot #J1007) provided by Hybritech Incorporated.

The assay was performed over 36 hours in the same manner as Reaction Two of Example B. Seven assays were performed with differing known concentrations of IgE (0 to 2400 IU/ml). The total volume of solution in each reservoir was 1.2 ml.

3. Results

Figure 6:
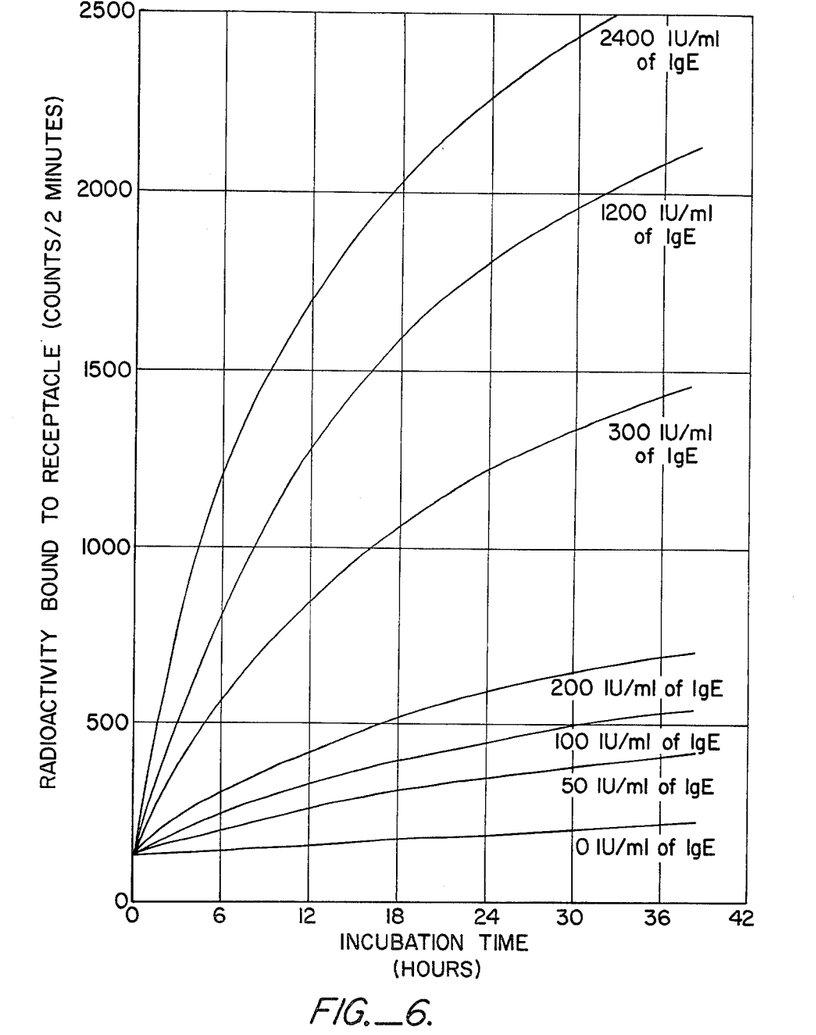

Referring to FIG. 6, the amounts of radioactivity bound to the reactive solid phases of seven individual receptacles are plotted against time. The results demonstrate a successive increase in radioactivity with time when antigen is present and show that by extrapolating each curve it is possible to predict the respective end-point radioactivities. The slopes of the lines, as well as their predicted end-points, are seen to be directly related to the amounts of non-radioactive (standard) IgE antigen in the solutions being assayed.

Thus, the method and apparatus of the present invention provide for relatively rapid assays achieved by periodic agitation of the sample solutions under pressure. Moreover, the ability to separate free from bound label allows the performance of rate mode or dynamic assays where the progress of the assay reaction can be observed over time.

Although the foregoing invention has been described in some detail by way of illustration and example for purposes of clarity and understanding, it will be obvious that certain changes and modifications may be practiced within the scope of the claims.

What is claimed is:

1. A method for determining an analyte which is a member of a specifically binding pair in a sample fluid, said method comprising:

introducing into a reaction zone comprising one member of the specifically binding pair immobilized within the interior of a receptacle having a single port (a) the sample fluid by immersing the receptacle port beneath the surface of the sample fluid and elevating the pressure surrounding the receptacle and (b) a labelling reagent comprising a detectable label conjugated to one member of a specifically binding pair by immersing the receptacle port beneath the surface of a solution of said reagent to entrap a fixed amount of gas in the receptacle, and elevating the surrounding pressure to introduce reagent into the receptacle and compress the gas until the pressure inside the receptacle substantially equals the surrounding pressure, whereby a portion of the labelling reagent becomes bound to the reaction zone, the extent of said portion being related to the amount of analyte in the sample fluid;

expelling the mixture of said sample fluid and said labelling reagent from the reaction zone by lowering the surrounding pressure; and detecting the amount of bound label.

2. A method as in claim 1, wherein the analyte and the substance in the reaction zone are analogous members of one specifically binding pair constituting a ligand and its receptor so that the analyte and the substance compete for binding to the labelled reagent comprising a complementary member of the specifically binding pair.

3. A method as in claim 1, wherein the analyte and the substance in the reaction zone comprise complementary members of one specifically binding pair so that the analyte is capable of binding directly to the bound substance in competition with the labelled reagent comprising a member of the specifically binding pair analogous to the analyte.

4. A method as in claim 1, wherein the analyte and the substance are members of different specifically binding pairs, so that the analyte binds to the substance through an intermediate binding substance which is capable of binding to both the analyte and the substance.

5. A method as in claim 4, wherein the receptacle includes the reaction zone and the intermediate binding substance is introduced into the reaction zone separately from the analyte by immersing the receptacle port beneath the surface of a solution containing said intermediate binding substance and thereafter elevating the pressure in the enclosure.

6. A method as in any of claims 2, 3, 4 or 5, wherein the pressure in the enclosure is periodically varied to agitate the sample fluid in the reaction zone so that the reaction time is reduced.

7. A method as in any of claims 2 or 3 further comprising periodically removing the sample fluid from the reaction zone and determining the extent of binding between the labelled reagent and the substance.

8. A method as in claim 4, wherein the reservoir includes the reaction zone and the intermediate binding substance is introduced to the reservoir separately from the analyte by means of the receptacle.

9. A method for determining in a sample fluid the presence of an analyte which is a member of a specifically binding pair consisting of a ligand and a receptor, said method comprising:

introducing into a receptacle having a single port (a) the sample fluid and (b) a labelled reagent comprising a detectable label conjugated to one member of the specifically binding pair by immersing the receptacle port beneath the surface of the sample fluid and the labelled reagent to entrap a fixed amount of gas therein, and elevating the surrounding pressure by a predetermined amount to introduce said sample fluid and reagent into the receptacle and thereby compress the gas until the pressure inside the receptacle substantially equals the surrounding pressure;

expelling the mixture of said sample fluid and said labelled reagent from the receptacle into a reservoir having a reaction zone comprising one member of the specifically binding pair immobilized therein by lowering the surrounding pressure whereby a portion of the labelled reagent becomes bound to the reaction zone, the extent of said portion being related to the amount of analyte in the sample fluid;

removing unbound labelled reagent from the reservoir by immersing the port beneath the surface of the fluid and elevating the surrounding pressure; and detecting the amount of the bound labelled reagent.

10. A method for determining in a sample fluid the presence of an analyte which is a member of a specifically binding pair, said method comprising:

immersing a port in an otherwise closed receptacle beneath the surface of said sample fluid to entrap a fixed amount of gas within the receptacle, said fluid sample being held in a reservoir which is located inside an enclosure;

manipulating the pressure within said enclosure to compress said fixed amount of entrapped gas and to transfer the sample fluid and a labelled reagent which is a member of a specifically binding pair between the reservoir and the receptacle to expose a reaction zone comprising an immobilized substance capable of reacting by non-covalent binding with said analyte to said fluid so that the amount of labelled reagent bound within the reaction zone is proportional to the amount of analyte present; and determining the extent of reaction between the analyte and the substance bound within the reaction zone by observing the amount of label bound within the reaction zone after the sample fluid has been exposed to the reaction zone for a predetermined amount of time.

11. An assay as in claims 9 or 10, wherein the sample fluid and the labelled reagent are mixed prior to being introduced simultaneously into the receptacle.

12. An assay as in claims 9 or 10, wherein the sample fluid and the labelled reagent are introduced separately into the receptacle.

13. An assay as in claims 9 or 10, wherein the analyte and the labelled reagent comprise the same member of the specifically binding pair and compete for binding to the reaction zone which comprises the other member of the specifically binding pair.

14. An assay as in claims 9 or 10, wherein the labelled reagent and the reaction zone comprise the same member of the specifically binding pair while the analyte comprises the complementary member, and wherein the analyte is introduced prior to introducing the labelling reagent.

15. In a method for determining an analyte in a sample fluid, wherein said sample fluid is introduced into a solid phase reaction zone and removed from said zone before measuring a signal related to the concentration of analyte, an improved method for transferring the fluid to and from said reaction zone, said method comprising:

immersing a port of a single port receptacle beneath the surface of a pool of the sample fluid held in a reservoir located in an enclosure so that a fixed amount of gas is entrapped in the receptacle, where at least one of said receptacle and said reservoir includes the reaction zone in its interior; and manipulating the pressure in the enclosure to compress said fixed amount of entrapped gas and to transfer the sample fluid between the reservoir and the receptacle so that a predetermined amount of sample fluid can be introduced to and withdrawn from the solid phase reaction zone.

16. An improved method for determining an analyte in a fluid as in claim 15, wherein the reaction zone is present in the receptacle and the pressure is first elevated a predetermined amount to cause a desired volume of the fluid to enter said reaction zone and thereafter lowered to substantially drain the reaction zone prior to determining the extent of reaction therein.

17. An improved method for determining an analyte as in claim 15, wherein the reaction zone is present in the reservoir and the pressure is elevated to remove unbound label from said reaction zone prior to determining the extent of the reaction therein.

18. An assay for simultaneously determining an analyte in a plurality of discrete sample fluid reservoirs, said analyte being a member of a specifically bindable pair, said assay comprising:

(a) immersing a port in a receptacle beneath the respective surface of each of the sample fluid reservoirs so that a fixed amount of gas is entrapped in said receptacle, each receptacle having a single port and substantially identical dimensions and including a reaction zone characterized by a reaction system which includes a member of the specifically binding pair bound within the reaction zone and produces a detectable signal related to the presence of analyte and a labelled reagent comprising a member of the specifically binding pair in the sample;

(b) simultaneously elevating the pressure on the surface of each of the samples to compress said fixed amount of entrapped gas so that a substantially identical amount of fluid enters each receptacle and contacts the reaction zone to complete the reaction system;

(c) lowering the pressure so that the fluid is discharged from each reaction zone and the reaction systems produce detectable signals related to the amount of analyte initially present in each sample fluid; and (d) measuring said signals.

19. An assay as in claim 18, further comprising repeating steps (a) through (d) in order to periodically determine the extent of reaction.

20. An assay as in claim 18, wherein the pressure on the surface of each of the samples is maintained uniform by keeping the samples in a common plenum and changing the pressure in the plenum.

21. An assay as in claim 20, wherein the pressure in the plenum is periodically varied to agitate the sample fluid in the reaction zone.

* * * * *